United States Patent
Abdelmagid et al.

(10) Patent No.: US 12,338,201 B2
(45) Date of Patent: Jun. 24, 2025

(54) PRODUCTION OF UREA AND MELAMINE

(71) Applicant: Stamicarbon B.V., Sittard (NL)

(72) Inventors: Ahmed Abdelmagid, Sittard (NL); Wilhelmus Hubertus Geurts, Born (NL)

(73) Assignee: Stamicarbon B.V., Sittard (NL)

( * ) Notice: Subject to any disclaimer, the term of this patent is extended or adjusted under 35 U.S.C. 154(b) by 0 days.

(21) Appl. No.: 18/553,330

(22) PCT Filed: Jul. 6, 2023

(86) PCT No.: PCT/NL2023/050364
§ 371 (c)(1),
(2) Date: Sep. 29, 2023

(87) PCT Pub. No.: WO2024/010450
PCT Pub. Date: Jan. 11, 2024

(65) Prior Publication Data
US 2024/0270684 A1 Aug. 15, 2024

(30) Foreign Application Priority Data
Jul. 7, 2022 (EP) .................................... 22183646

(51) Int. Cl.
| C07D 251/62 | (2006.01) |
| C07C 273/04 | (2006.01) |
| C07C 273/12 | (2006.01) |
| C07C 273/16 | (2006.01) |
| C07D 251/60 | (2006.01) |

(52) U.S. Cl.
CPC .......... *C07C 273/12* (2013.01); *C07C 273/04* (2013.01); *C07C 273/16* (2013.01); *C07D 251/60* (2013.01); *C07D 251/62* (2013.01)

(58) Field of Classification Search
CPC ... C07C 273/12; C07C 273/04; C07C 273/16; C07D 251/62; C07D 251/60
See application file for complete search history.

(56) References Cited

U.S. PATENT DOCUMENTS 5,767,313 A   6/1998   Jonckers

FOREIGN PATENT DOCUMENTS

| WO |        02090323 A1 | 11/2002 |
| WO |    2008052640 A1   |  5/2008 |
| WO |    2015093942 A1   |  6/2015 |
| WO | WO 2023/280684 A1 * | 1/2023 |

OTHER PUBLICATIONS

International Search Report and Written Opinion for corresponding International Application No. PCT/NL2023/050364, dated Sep. 13, 2023.

\* cited by examiner

*Primary Examiner* — Bruck Kifle
*Assistant Examiner* — Kevin S Martin
(74) *Attorney, Agent, or Firm* — Leason Ellis LLP

(57) ABSTRACT

The disclosure pertains to a process for the production of urea and melamine, wherein off-has from a high pressure melamine plant is combined with a urea liquid obtained from flashing of a urea synthesis solution. Also disclosed is a system for the combined production, and the modification of an existing plant or system.

24 Claims, 5 Drawing Sheets

PRODUCTION OF UREA AND MELAMINE

CROSS-REFERENCE TO RELATED PATENT APPLICATIONS

This application is a U.S. National Stage Application under 35 U.S.C. § 371 of International Patent Application No. PCT/NL2023/050364 filed Jul. 6, 2023, which claims the benefit of priority of European Patent Application No. 22183646.3 filed Jul. 7, 2022, both of which are incorporated by reference in their entireties.

FIELD

The invention pertains to the combined production of urea and melamine, whereby off-gas from the production of melamine is used as a feed to the synthesis of urea. Particularly, the invention pertains to an integrated process and system for the production of urea and melamine.

BACKGROUND

Urea is generally produced from ammonia and carbon dioxide. Thereby carbon dioxide and ammonia are reacted in a high pressure (HP) urea synthesis section, forming a urea synthesis solution. In understanding various aspects of a urea process and production plant, it is generally instructive to understand the underlying reactions. Ammonia and carbon dioxide first react to form ammonium carbamate, according to the exothermic reaction:

$$2NH_3 + CO_2 \longrightarrow H_2N-CO-ONH_4.$$

In a second step, the formed ammonium carbamate is dehydrated to give urea according to the endothermic equilibrium reaction:

$$H_2N-CO-ONH_4 \longleftrightarrow H_2N-CO-NH_2 + H_2O.$$

The formed urea synthesis solution is subjected to recovery of unreacted ammonia and carbon dioxide. This can be accomplished in several ways, which generally applied in various combinations in a urea plant. Thus, in a urea stripping plant, the urea synthesis solution is subjected in a HP section to stripping and condensation of thereby recovered ammonia and carbon dioxide. The, e.g. stripped, urea synthesis solution is subjected to further recovery of unreacted ammonia and carbon dioxide in one or more urea recovery sections, parallel and/or in series, and operated at medium (MP) and/or low (LP) pressure. The recovered ammonia and carbon dioxide ultimately are recycled, as an ammonium carbamate solution, to the synthesis section, thereby completing a urea synthesis loop. The urea solution is generally subjected to evaporation so as to form a highly concentrated solution that is generally referred to as a urea melt. The urea melt can be put to use in a connected plant, such as a melamine plant, and/or it can be subjected to finishing into a solid form, such as prills or granules.

The challenges in the aforementioned recovery processes generally are to separate out unreacted ammonia and carbon dioxide as efficient as possible, and recycling these with as low an amount of water as possible. The latter is important, since, as follows from the aforementioned second reaction step, the presence of water will adversely shift the equilibrium to the carbamate side. To this end, inter alia, the various recovery stages generally involve treatment steps in which a urea solution is subjected to decomposition (dissociation) of still present ammonium carbamate into its components ammonia and carbon dioxide, which components are subsequently condensed and further recycled. In respect of the recycling of ammonium carbamate, it is to be understood that ammonium carbamate requires a minimum amount of water to remain dissolved, said required amount increasing with decreasing pressure.

Further factors generally taken into account in the various recovery and recycle steps, are the efficient use of energy, e.g. with reference to the heat required for carbamate decomposition, and the recycle ratio of the N (ammonia) and C (carbon dioxide components. In respect of the latter, it is to be understood that the urea-forming reaction involves an N:C ratio of 2:1, but the overall ratio with which the urea synthesis section is carried out, generally involves an excess of ammonia, e.g. an N:C ratio of 3:1.

Melamine is regularly produced from urea, thereby yielding an off-gas (hereinafter also indicated as "melamine off-gas") comprising ammonia and carbon dioxide as by-products, in the aforementioned 2:1 molar ratio utilized in the urea-forming reaction. Generally two types of melamine production processes exist. One is a catalytic "low pressure" process, which applies atmospheric pressure (from atmospheric pressure to about 70 bar). The other is called a "high pressure" process. In melamine production, high pressure refers to a pressure of at or above about 70 bar (7 MPa), more typically at or above 80 bar (8 MPa).

It is well-known in the art to combine the production of urea and the production of melamine. Thereby, generally, at least part or all of the urea produced in a urea production plant, is sent to a melamine plant as a starting material. Thus, the integrated production of urea and melamine typically involves feeding the off-gas obtained from the melamine plant, directly or indirectly, to the synthesis section of the urea plant.

An on-going challenge in the field, concerns finding a suitable position for allowing the melamine off-gases to enter the urea synthesis loop. A particular issue with the off-gases from high-pressure melamine processes, is that these have a pressure that does not match the pressure of operation in any of the customary sections of a urea production plant. The off-gas produced in a high-pressure melamine synthesis process is initially obtained at synthesis pressure, which is generally at least 70 bar, and frequently in a range of from 80 to 150 bar. This pressure in many cases is lower than that of a HP urea synthesis section, which is generally in a range of from 120 to 400 bar, and more typically 140 to 160 bar. Further, in some cases, the off-gas from melamine synthesis is not actually released at synthesis pressure, but at a lower pressure, typically 2-30 bar, such as 20-25 bar. This is typically accomplished as a result of downstream processing or work-up, such as a washing step, as a result of which the off-gas as released at lower pressure comprises a substantial amount of water, such as 3 to 40% by weight and more specifically between 5 and 30% by weight, next to the ammonia and carbon dioxide. It has been known to recycle these off-gases to an MP section, either already present in a urea plant, or otherwise presented in an integrated plant coupling both of the production processes.

A method of this type is disclosed in WO2008/052640. In this process the off-gas gas stream from the melamine plant is condensed, together with a recycle ammonium carbamate solution, in a condensation section of a medium pressure treatment section of the urea plant. This presents a passive method that generally serves to recycle the melamine off-gas to urea synthesis.

It is desired to make a different, or even better, use of the melamine off-gas as an active component in the carbamate recovery and/or to make better use of the available energy of the off-gas.

SUMMARY

In order to better address one or more of the foregoing desires, the invention, in one aspect provides a process for the production of urea and melamine, wherein the production of urea comprises subjecting ammonia and carbon dioxide to a urea-forming reaction in a high-pressure urea synthesis section so as to obtain a high pressure urea synthesis solution, subjecting the urea synthesis solution to flashing, preferably at medium pressure, resulting in a flash vapour comprising ammonia and carbon dioxide, and a flashed urea liquid; subjecting the flashed urea liquid to treatment, preferably in a medium pressure treatment section, so as to obtain a urea product solution, preferably a medium pressure urea product solution, and a carbamate recovery vapour, preferably a medium pressure carbamate recovery vapour, said treatment comprising one or more ammonia and carbon dioxide liberating steps, thereby removing ammonia and carbon dioxide vapour from the flashed urea liquid, wherein the production of melamine comprises subjecting urea to a non-catalytic, high pressure melamine forming reaction, so as to obtain melamine and a melamine off-gas comprising ammonia and carbon dioxide; and wherein the combined process comprises contacting at least part of the melamine off-gas with the flashed urea liquid before or during at least one of said ammonia and carbon dioxide liberating steps.

In another aspect, the invention presents a system for the production of urea and melamine, said system comprising a urea production zone; said urea production zone comprising a high pressure urea synthesis section and, downstream thereof and in fluid communication therewith, a urea recovery section adapted to separately obtain a urea solution and a carbamate recovery stream; the system further comprising a melamine production zone; said melamine production zone comprising a high pressure melamine synthesis section, said production zones being connected with each other so as to allow transport of melamine off-gas obtained from the melamine synthesis section to the urea production zone, whereby the urea production zone comprises a medium or low pressure treatment section adapted to receive said melamine off-gas, said treatment section comprising a flashing unit and at least one ammonia and carbon dioxide liberating unit, said flashing unit having an inlet for urea synthesis solution connected to an outlet of the high pressure synthesis section via a pressure reducing device, an outlet for flash vapour and an outlet for flashed liquid, said ammonia and carbon dioxide liberating unit having an inlet for flashed liquid connected to the outlet for flashed liquid from the flashing unit, an outlet for carbamate recovery vapour and an outlet for a urea product stream, said outlets for flash vapour and carbamate recovery vapour each being connected via a condensation and recirculation circuit to the urea synthesis section, wherein an outlet for melamine off-gas from the melamine synthesis section is in fluid communication with an inlet of at least one ammonia and carbon dioxide liberating unit, allowing the melamine off-gas to be contacted with flashed liquid in or upstream of the ammonia and carbon dioxide liberating unit.

In yet another aspect, the invention concerns a method for the modification of a pre-existing urea plant comprising a high pressure urea synthesis section and, downstream thereof and in fluid communication therewith, a urea recovery section adapted to separately obtain a urea solution and a carbamate recovery stream, the method comprising connecting the urea plant with a melamine plant comprising a high pressure melamine synthesis section so as to allow recirculation of melamine off-gas from the melamine off-gas treatment section to the urea plant, the method comprising adding a medium or low pressure treatment section adapted to receive said melamine off-gas, said treatment section comprising a flashing unit and at least one ammonia and carbon dioxide liberating unit, said flashing unit having an inlet for urea synthesis solution connected to an outlet of the high pressure synthesis section via a pressure reducing device, an outlet for flash vapour and an outlet for flashed liquid, said ammonia and carbon dioxide liberating unit having an inlet for flashed liquid connected to the outlet for flashed liquid from the flashing unit, an outlet for carbamate recovery vapour and an outlet for a urea product stream, said outlets for flash vapour and carbamate recovery vapour each being connected via a condensation and recirculation circuit to the urea synthesis section, wherein an outlet for melamine off-gas from the melamine synthesis section is in fluid communication with an inlet of the ammonia and carbon dioxide liberating unit, allowing the melamine off-gas to be contacted with flashed liquid in or upstream of the ammonia and carbon dioxide liberating unit.

In a still further aspect, the invention provides a method for the modification of a pre-existing system for the production of urea and melamine, said pre-existing system comprising a urea production zone and a melamine production zone; said urea production zone comprising a high pressure urea synthesis section in fluid communication with a urea recovery section adapted to separately obtain a urea solution and a carbamate recovery stream, said recovery section comprising a medium or low pressure treatment section comprising a flashing unit and an ammonia and carbon dioxide liberating unit, said flashing unit having an inlet for urea synthesis solution connected to an outlet of the high pressure synthesis section via a pressure reducing device, an outlet for flash vapour and an outlet for flashed liquid, said ammonia and carbon dioxide liberating unit having an inlet for flashed liquid connected to the outlet for flashed liquid from the flashing unit, an outlet for carbamate recovery vapour and an outlet for a urea product stream, said outlets for flash vapour and carbamate recovery vapour each being connected via a condensation and recirculation circuit to the urea synthesis section, said melamine production zone comprising a high pressure melamine synthesis section and, downstream thereof and in fluid communication therewith, a melamine off-gas treatment section for obtaining melamine off-gas of reduced pressure; said production zones being connected with each other so as to allow transport of melamine off-gas from the melamine off-gas treatment section to a the urea production zone, and optionally also to allow transport of urea from the urea production zone to the melamine synthesis section, the method comprising providing a connection between an outlet for melamine off-gas from the melamine synthesis section to an inlet of the ammonia and carbon dioxide liberating unit, allowing the melamine off-gas to be contacted with flashed liquid in or upstream of the ammonia and carbon dioxide liberating unit.

DETAILED DESCRIPTION

Figure 1:
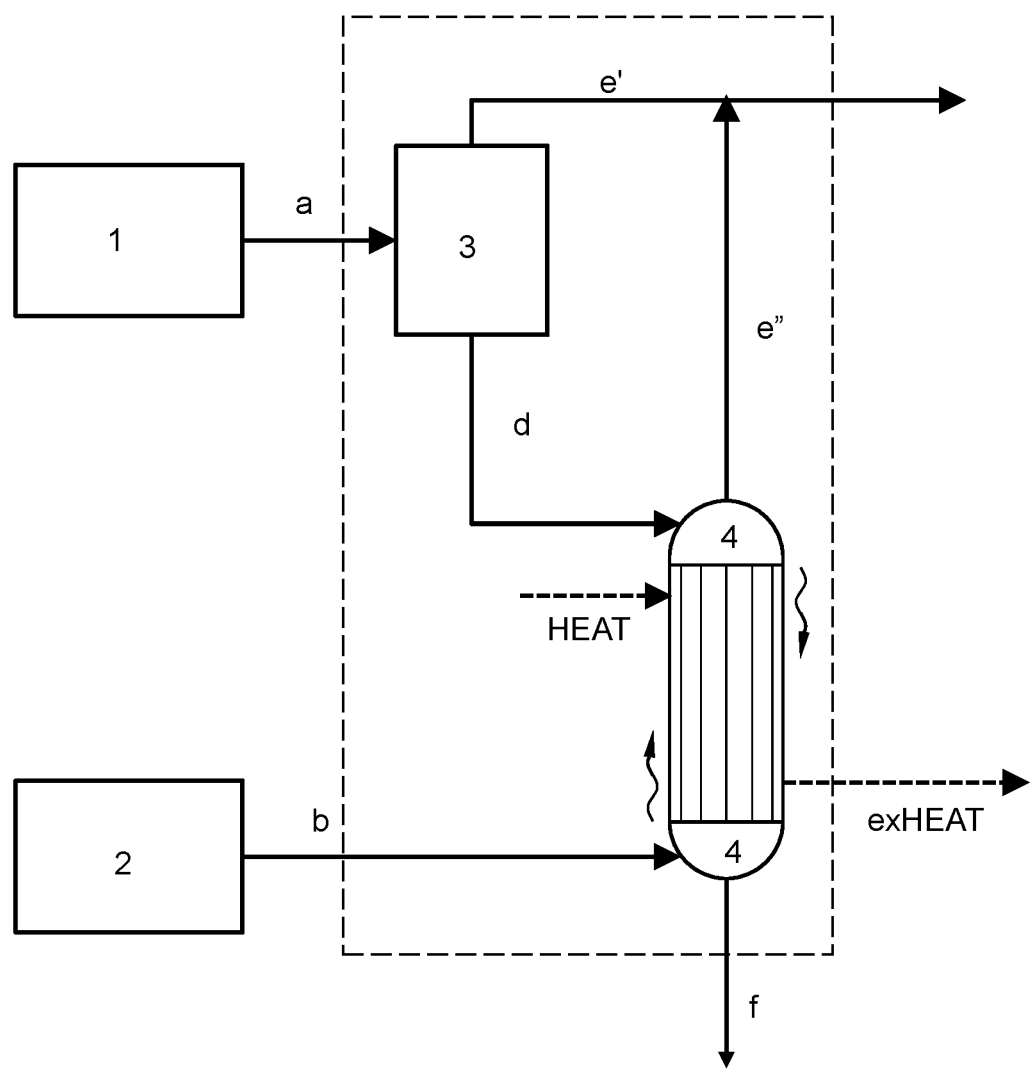
FIG. 1, FIG. 2, and FIG. 3 are schematic drawings of embodiments of system for the production of urea and melamine.

The invention is based on the judicious insight to utilize the sensible heat of the off-gas from high pressure melamine production, in supporting the decomposition of carbamate present in a urea synthesis solution. To this end, the off-gas is combined with urea liquid, obtained from the flashing of a urea synthesis solution. This is in marked deviation from existing processes for the combined production of urea and melamine, in which melamine off-gas is generally sent to a condensation step in the urea production process.

The flashing of a liquid, such as a urea synthesis solution, implies the expansion of such liquid at a pressure below the original pressure. The urea synthesis solution originates from a section operating at high pressure (HP). In the context of a urea production process and plant, the flashing occurs in a section operating at medium (MP) or low (LP) pressure. These terms each have a well-established meaning in the field of urea production. HP indicates generally a pressure of from 12-40 MPa (120 to 400 bar), preferably 140 to 160 bar. MP in urea production generally indicates pressures in a range of from 1 MPa to 8 MPa, preferably 1 MPa to 4 MPa (10-40 bar), more preferably 15 to 35 bar, and most typically 20 to 25 bar. LP in urea production stands for pressures below 1 MPa, preferably 0.3-0.5 MPa (3-5 bar), typically about 4 bar.

In respect of melamine production the term "HP" generally indicates at or above 7 MPa (70 bar), preferably at or above 8 MPa (80 bar), and more preferably 80 to 150 bar.

In the present process at least part of the melamine off-gas is contacted with a flashed urea liquid in one or more ammonia and carbon dioxide liberating steps. Urea production processes generally comprise such steps in order to optimize the recovery of unreacted ammonia and carbon dioxide. Such unreacted ammonia and carbon dioxide is present in a urea synthesis solution in the form of water-soluble ammonium carbamate. In various stages of a urea production process, therefore, ammonia and carbon dioxide are liberated from the urea synthesis solution, generally removed as vapours and, ultimately recirculated to urea synthesis.

Generally, such ammonia and carbon dioxide liberating steps require a driving force to shift the equilibrium between dissolved ammonium carbamate and ammonia and carbon dioxide vapours, to more strongly favour the latter. One way to accomplish this, is by thermal decomposition (or, put otherwise, dissociation) of the ammonium carbamate, thereby enabling gaseous ammonia and carbon dioxide to be removed. Another way is by applying a stripping gas to the liquid, so as to remove carbon dioxide and ammonia vapours. Frequently, both heat and a stripping gas are applied. This is all well-known to the skilled person, and does not require elucidation here.

In the process of the invention, the melamine off-gas is contacted with the flashed urea liquid in an ammonia and carbon dioxide liberating step. This contacting can contribute to either or both of the aforementioned phenomena.

The off-gas from a high-pressure melamine process, has a higher temperature than the urea solution obtained from flashing a urea synthesis solution at medium or low pressure. Accordingly, the off-gas will act as a direct heating agent when introduced into the flashed urea liquid.

The flashing is conducted at medium or low pressure, generally at a pressure of 3 to 80 bar. Flashing at medium pressure (MP flashing) is generally preferred. This preference relates to the general notion that the purposes of treatment steps such as flashing, is to recover and recirculate (generally as ammonium carbamate) unreacted ammonia and carbon dioxide to urea synthesis. In view of the urea synthesis equilibrium, it is generally preferred to recirculate as low an amount of water as possible to urea synthesis. The condensation of flashed vapours at medium pressure requires a lower amount of water than the condensation of flashed vapours at low pressure. The flashing is preferably conducted at 10-70 bar, preferably at 10-35 bar, for instance 18-25 bar.

The flashing is preferably operated at a pressure that is equal to or higher than the pressure of the ammonia and carbon dioxide liberating unit, e.g. at a pressure 0-10 bar higher than the pressure of the ammonia and carbon dioxide liberating unit, e.g. 0-7 bar higher, preferably 0-7 bar higher, and more preferably at a pressure equal to the pressure at which the ammonia and carbon dioxide liberating unit is operated. The temperature of the flashed urea liquid (i.e., the liquid temperature downstream of the unit in which the flashing occurs) correlates with the pressure. Typically, at a flash pressure of 3 bar, said temperature is 100° C., at a flash pressure of 10 bar, the temperature is 127° C., and at a flash pressure of 70 bar, the temperature is 165° C. Preferably, the flash is conducted at 20-30, such as at 25 bar. At 25 bar, the temperature of the flashed liquid is 148° C. Pressures expressed in bar refer to the absolute pressure values (bara).

The melamine off-gas can also be introduced into the flashed urea liquid in such a way that it effectively acts as a stripping gas. This can possibly be accomplished in an apparatus designed as a stripping unit, such as a tray column or a packed column, or generally in a unit comprising a packed bed.

The discussed contacting takes place in an ammonia and carbon dioxide liberating step. This generally is conducted in a corresponding treatment unit, i.e., an ammonia and carbon dioxide liberating unit, such as a heating unit (typically a heat exchanging unit), a packed bed, or a combination thereof. Such a unit has an inlet for liquid, i.e., in this case a flashed urea liquid, an outlet for treated liquid, and an outlet for gas, enabling the removal of ammonia and carbon dioxide, i.e., carbamate recovery vapour. The unit further is designed such as to provide heat and or stripping, as discussed above. In the event that the ammonia and carbon dioxide liberating unit is a heater, this will generally be in the form of a shell and tube heater, many different designs of which are known to the skilled person. Herein the medium to be heated is in one compartment (such as the tube side), whilst a heat exchanging medium is provided in another compartment (such as the shell side). Typically, the medium to be heated, in this case a flashed urea liquid, will be passed via the tube side, whilst an external heating medium, such as a hot liquid or steam, will flow at the shell side. The liberation of ammonia and carbon dioxide necessarily involves decomposition (dissociation) of carbamate. The ammonia and carbon dioxide liberating unit therefore sometimes is also indicated as a decomposer or a dissociator. Unless indicate otherwise, in this description the terms "heating unit", "heat exchanging unit", "heater", such as "MP heater", "decomposer", such as "MP decomposer" and "dissociator", such as "MP dissociator" are all used interchangeably with the term "ammonia and carbon dioxide liberating unit." In an embodiment, the ammonia and carbon dioxide liberating unit can be a packed bed. Such a packed bed can be operated with heat, with a stripping gas for adiabatic stripping (e.g. carbon dioxide), or both. In the present invention the melamine off-gas can provide heat as well as act as a stripping gas over such packed bed. Packed beds are known in the industry, and its possible structures and materials (e.g. metal, ceramics, glass) do not require elucidation here.

In view of its higher temperature and pressure, the melamine off-gas introduced into the flashed urea solution, will directly transfer heat to this solution, thereby aiding decomposition of ammonium carbamate. The off-gases of melamine production thus are judiciously present in the same compartment, expressly in contact with the solution to be heated (typically the tube side of a shell-and-tube heat exchanger, whilst steam or hot liquid can be additionally provided at the shell side). Depending on the precise conditions and heat requirements, it is conceivable in the present process that an ammonia and carbon dioxide liberating unit into which hot melamine off-gas is injected, is operated with or without an external heating medium.

The skilled person will be able to determine the precise heat requirements on the basis of the heat and pressure of the melamine off-gas, and the conditions in the medium or low pressure ammonia and carbon dioxide liberating step, or steps, concerned.

The off-gas produced in a high-pressure melamine synthesis process is initially obtained at synthesis pressure, which is generally at least 70 bar, and frequently in a range of from 80 to 150 bar. When introduced into a medium-pressure (MP) or low pressure (LP) section of a urea plant, the pressure of the melamine off-gas is lowered by an expansion valve at the inlet of said MP or LP section. A typical condition for the melamine off-gas introduced into the ammonia and carbon dioxide liberating unit is 250° C. at 80 bar. In some types of melamine production plants, which are also generally suitable for conducting the presently disclosed method, the melamine off-gas is discharged at a pressure between 10 and 70 bar, preferably between 20 and 30 bar, for example 25 bar.

The temperature of the off-gas obtained from a high-pressure melamine synthesis section, can widely vary. Generally, such melamine off-gas is discharged at a temperature of from 140° C. to 400° C., such as from 150° to 300° C. Preferably, the temperature is above 160° C., more preferably above 175° C. Preferably, the temperature is below 285° C., more preferably below 275° ° C. Most preferably, the temperature is in a range of from 200° C. to 250° C., such as 210° C. to 240° C., such as 215° ° C. to 235° C. It will be understood that in conducting the method of the present invention, the melamine off-gas prior as brought into contact with the flashed urea liquid, has a temperature above that of said liquid.

By the introduction of the melamine off-gas into a urea solution during an ammonia and carbon dioxide liberating step, the available heat from the HP melamine off-gas is well used, whilst less heat needs to be provided by a heat exchanging medium (typically steam or a hot liquid stream such as a condensate).

Typically, the ammonia and carbon dioxide liberating step, particularly bringing about dissociation of ammonium carbamate, is conducted in an MP or LP heating unit which is a shell-tube heat exchanger, whereby the medium to be heated is in one compartment (such as the tube side), whilst the heat exchanging medium is provided in another compartment (such as the shell side). The off-gases of melamine production, however, are judiciously present in the same compartment, expressly in contact with the solution to be heated (typically the tube side of a shell-and-tube heat exchanger, whilst steam or hot liquid, to the extent desired, is additionally provided at the shell side). The introduction of the melamine off-gas into the urea liquid can be conducted co-currently with the flow of the urea liquid, or counter-currently.

It will be understood that in the present process, the melamine off-gas interacts with the flashed urea liquid in the course of an ammonia and carbon dioxide liberating step, notably a stripping step and/or, preferably, a decomposition step. Said step results in both a liquid output and a gaseous output. The liquid output can be considered a medium or low pressure urea product solution. It is also conceivable that the ammonia and carbon dioxide liberating step is not a single step, but involves a plurality of subsequent steps. This can be, e.g., conducted in a plurality of heating units (such as a medium pressure dissociation unit), or in a combination of one or more heating units and a unit in which stripping takes place. The latter can refer to stripping upstream of decomposition (as discussed below) or downstream thereof (which is a typically existing configuration, e.g., as disclosed in WO 02/090323).

In the event of a plurality of subsequent ammonia and carbon dioxide liberating steps, the liquid input into the first of such steps is the flashed urea liquid proper. Such first step results in a liquid originating from the flashed urea liquid, but from which some ammonia and carbon dioxide has been removed. For the sake of convenience, in this description the liquid originating from the flashed urea liquid, subjected to a plurality of subsequent ammonia and carbon dioxide liberating steps, is indicated as being a "flashed urea liquid" in each such subsequent step. The liquid output of a final medium (or low) pressure ammonia and carbon dioxide liberating step, is indicated to be a "medium (resp. low) pressure urea product solution." This solution will be further treated a generally done in the art, such as, particularly, being sent to a low pressure recovery section.

In the event of a plurality of subsequent ammonia and carbon dioxide liberating steps, the melamine off gas can be introduced into the flashed urea liquid in any one or more of these steps. The gaseous output of each of these steps is hereby indicated as being a carbamate recovery vapour.

It will be understood that the purpose of obtaining carbamate recovery vapours, is to, ultimately, recirculate the recovered ammonia and carbon dioxide to the urea synthesis. Such recirculation generally involves condensing the carbamate recovery vapour at medium or low pressure, resulting in an MP or LP carbamate solution. The latter will generally be recirculated via one or more further treatments steps, particularly low pressure recovery steps, according to technology well available in the art.

The resulting condensate will be further processed so as to ultimately be recirculated to the HP synthesis section, involving one or more compression steps as appropriate.

It is noted that the flashed vapour from flashing a urea HP synthesis solution have a high N/C ratio, due to the 2:1 reaction being carried out with the presence of an excess ammonia present during synthesis, as mentioned above. Generally, therefore, upon further treating the carbamate recovery vapours generally carbon dioxide is added to adjust the N/C ratio during recirculation. A suitable option for such $CO_2$ addition is via an MP stripper, in which the carbamate recovery vapour is subjected to $CO_2$ stripping.

Generally, it is possible for melamine production to result, in addition to the aforementioned off-gas, also in a liquid carbamate stream, e.g., by condensation of part of the off-gas in a melamine plant. Such streams can be recycled to urea production, its preferred location depending on the composition of the stream (e.g., some melamine processes produce a stream comprising 40% of ammonia, 40% of carbon dioxide (i.e., 80% of carbamate) and 20% of water. It is also conceivable that a more lean carbamate stream is produced (such as 50% carbamate and 50% water). In addition to the recycling, according to the present invention, of the gaseous effluent of melamine production, such additional liquid effluent can generally be recycled to urea production as well, e.g., to a low-pressure recovery section.

The feature linking the melamine and urea production processes according to the invention, effectively is the MP or LP, and preferably MP, decomposition of a flashed urea synthesis solution. It will be understood that the flashed nature of this solution, which removes ammonia and carbon dioxide vapours, enables the addition of the further amounts of ammonia and carbon dioxide as are obtained from the melamine production process. Accordingly, the process is applicable to any urea production zone in which a urea synthesis solution is subjected to MP or LP flashing.

The process as described above combines the production of urea and melamine by using the melamine off-gas in the urea production. Preferably, a further integration of both processes involves using some or all of the urea produced, as the starting material for the melamine production. This can refer to an integrated plant having urea and melamine production zones, the mutual capacities of which are adapted to each other. It is also possible, that the melamine production has a relatively higher production capacity, e.g., by being fed with urea also from a further urea plant. This will enable sending an even larger amount of melamine off-gas to the urea plant. Considering the heat requirements in the ammonia and carbon dioxide liberating step or steps in urea production, it will generally have a greater benefit if a larger amount of off gas from HP melamine production is available to be combined with flashed urea liquid in urea production.

As is generally the case for a urea production process, the process comprises subjecting ammonia and carbon dioxide to urea-forming reaction in a reactor of a high-pressure urea synthesis section of a urea production zone (such as a urea production plant) so as to obtain a urea synthesis solution.

With reference to the linking feature mentioned above, the carbamate recovery in the process according to the invention, comprises subjecting a urea synthesis solution to flashing at medium pressure (MP). Preferably, in one embodiment, this solution is the solution as obtained from HP stripping. This stripping can be done with ammonia as a stripping medium, with only supply of heat ("self-stripping") or, particularly, with carbon dioxide or ammonia, and with heat. The most widely used stripping process today, is the Stamicarbon stripping process, applying $CO_2$ as the stripping medium, effectively introducing at least part of the $CO_2$ as a feed for the urea synthesis, via the HP stripper. The HP stripping results in the removal of an initial amount of unreacted ammonia and carbon dioxide, which is thereupon subjected to condensation in a HP carbamate condenser. After which the condensate is recirculated to the reactor. The stripped urea solution, which also contains ammonium carbamate, is subjected to further recovery of ammonia and carbon dioxide at medium and low pressure.

It will be understood that also the aforementioned flash vapour and carbamate recovery vapour will eventually be recirculated to urea synthesis. The flash vapour and the carbamate recovery vapour generally will each be subjected to condensation, in separate MP and/or LP condensation sections or in the same MP or LP condensation section. Such condensation sections comprise at least one condenser, such is two condensers. Preferably, the flash vapour and the carbamate recovery vapour are sent to the same condenser, preferably to an MP condenser. The resulting condensate will be further processed so as to ultimately be recirculated to the HP synthesis section. This can be directly, involving an appropriate compression step, or the condensate can advantageously be mixed with LP carbamate recirculated from the LP recovery section. As the person skilled in urea production will be aware, LP carbamate necessarily contains a relatively high amount of water. In order to desirably reduce the amount of water transferred to urea synthesis, the present process enables increasing the concentration of the LP carbamate, by mixing it with condensate obtained from the carbamate recovery vapours. In a preferred embodiment thereof, the carbamate recovery vapours are condensed together with the LP carbamate in a single condenser. Alternatively, the vapours from the flash can be condensed separately in a first condenser and the carbamate recovery vapours can be combined with LP carbamate and condensed in a second condenser.

The process of the invention preferably involves using urea produced in the urea production process as a starting material in the melamine synthesis. Depending on the mutual production capacities, this can be all of the urea produced in the urea production zone, or a part of it. E.g., the invention can be put to use in the context of dedicated urea production, wherein the capacity of a urea production zone or plant matches the capacity of a connected melamine production zone or plant. In a generally preferred set-up, the capacity of the urea production zone or plant exceeds that of the melamine production zone or plant. Thereby, a part of the produced urea is sent to melamine production and a part is provided to one or more urea finishing processes, to produce solid urea, such as prilling or granulation, or liquid urea is provided to a process for making Diesel Exhaust Fluid, and/or urea is applied to the production of products such as urea ammonium sulphate or urea ammonium nitrate. Depending on the capacity requirements for producing such urea products, it will be understood that the connected melamine production can also be fed, wholly or partly, and possibly temporarily, with urea sourced from elsewhere.

As the skilled person will be aware, the urea solution obtained from urea recovery will generally be subjected to concentration prior to being used as a starting material in melamine synthesis. This concentration will preferably occur to the extent that a highly concentrated urea solution is formed (e.g. having more than 90 wt. % of urea, such as more than 95 wt. % of urea, such as more than 99 wt. % of urea) for which the term "urea melt" is used in the art. It will be understood that such concentration occurs between urea recovery and melamine synthesis, and preferably in an evaporation section of the urea plant. Typically, the urea solution is concentrated in an evaporation section to a urea melt having a final moisture content of 0.2-5.0% by weight.

In the event that not all of the produced urea is used in the melamine production, the remainder of the urea, particularly of the urea melt, can be subjected to regular urea finishing, e.g. obtained as granules or prills.

Also, urea not sent to melamine synthesis, can be obtained as an aqueous solution, such a solution having 30-35 wt. % of urea and of sufficient purity so as to be suitable as so-called Diesel Exhaust Fluid (DEF). These and other finished urea products are known to the skilled person, and do not require elucidation here.

The invention also pertains to a system for the production of urea and melamine in accordance with the method as described above. Said system comprises a urea production zone. This can be a separate urea plant, or it can be a zone that is part of an integrated plant for the production of urea and melamine. The urea production zone comprises a high pressure urea synthesis section and, downstream thereof and in fluid communication therewith, a low pressure urea recovery section adapted to separately obtain urea and an aqueous carbamate solution. The system also comprises a melamine production zone which, again, can be a separate plant or a zone comprised in an integrated plant. The melamine production zone comprises a high pressure melamine synthesis section. It will be understood that the term "high pressure" has different meanings in respect of the urea production zone and the melamine production zone, as explained hereinbefore.

The production zones are connected with each other so as to allow transport of melamine off-gas obtained from the high pressure melamine synthesis section to the urea production zone, whereby the urea production zone comprises a medium or low pressure treatment section adapted to receive said melamine off-gas, preferably a medium pressure treatment section. In accordance with the invention, and in view of the process described hereinbefore, said treatment section comprising a flashing unit and at least one ammonia and carbon dioxide liberating unit.

The flashing unit has an inlet for urea synthesis solution connected to an outlet of the high pressure synthesis section. Since this concerns a connection from a HP section to an MP or LP section, the HP urea synthesis solution will necessarily leave the HP section via a pressure reducing device, typically a pressure-reducing valve. The flashing unit has an outlet for flash vapour and an outlet for flashed liquid. The ammonia and carbon dioxide liberating unit has an inlet for flashed liquid connected to the outlet for flashed liquid from the flashing unit, an outlet for carbamate recovery vapour and an outlet for a urea product stream. As discussed above, the MP and/or LP treatment section of the urea production zone can comprise more than one ammonia and carbon dioxide liberating unit.

The outlets for flash vapour and carbamate recovery vapour are each connected via a condensation and recirculation circuit to the urea synthesis section. As mentioned with reference to the process above, this can involve a connection to separate condensation sections for the flash vapour and the carbamate recovery vapour, or the respective outlets can be connected to the same condensation section. A condensation section optionally comprises more than one condenser, such as two or more condensers in series, and/or parallel.

In accordance with the invention, an outlet for melamine off-gas from the melamine synthesis section is in fluid communication with an inlet of at least one ammonia and carbon dioxide liberating unit, such as a heating unit. This allows the melamine off-gas to be contacted with flashed liquid in said unit. It will be understood that the ammonia and carbon dioxide liberating unit or units will have a gaseous output, which is the aforementioned carbamate recovery vapour. Accordingly, each ammonia and carbon dioxide liberating unit has an outlet for carbamate recovery vapour.

The ammonia and carbon dioxide liberating unit can be designed as a stripping unit (preferably and MP stripper), as a heating unit (preferably an MP heater), or both. The indication of pressure (MP and/or LP) generally refers to the pressure under which the equipment is operated. At the same time, this also presents the skilled person with design requirements, e.g. the MP equipment should be able to withstand at least the MP range as defined in urea production. It will be understood that such equipment is well-known in the urea field, and can be designed to meet the MP requirement without difficulty. Such designs are fully known to the skilled person, as are designs for HP and LP equipment. Preferably, the flashed liquid is sent to the ammonia and carbon dioxide liberating unit via a rectifying column. Such rectifying column receives, counter currently with the liquid flow, carbamate recycle vapours from the ammonia and carbon dioxide liberating unit.

In an interesting embodiment, a packed bed is provided downstream of the flashing unit, typically provided in a rectifying column, and upstream of a heating unit. In this embodiment, the packed bed can have an inlet for at least part of the melamine off-gas. This inlet is optionally positioned such that the melamine off-gas is contacted counter-currently, with flashed urea liquid flowing over the packed bed. By virtue of the increased surface area provided by the packed bed, the melamine off-gas in this embodiment acts as a stripping gas for the flashed urea liquid, thus providing carbamate recovery vapour resulting from stripping.

Preferably, the flashing unit, the rectifying column, optionally also containing a packed bed, and the ammonia and carbon dioxide liberating unit are contained in a single apparatus. This apparatus comprises, at its upper end, a flash vessel, below the flash vessel a rectifying column, optionally provided with a packed bed, and at its lower end a heating unit. The single apparatus can have one or more inlets for melamine off-gas, e.g., in the heating unit and/or at the packed bed, and can provide for counter-current or co-current flow of the melamine off-gas and the flashed urea liquid. In a preferred embodiment, the apparatus has a single inlet for melamine-off gas, at the downstream side of the heating unit. This has been found to result in a still more effective use of the heat from the melamine off-gas. Without wishing to be bound by theory, the inventors believe that the off-gas introduced this way into the flashed urea liquid, causes a turbulence which aids in the liberation of ammonia and carbon dioxide. As a result of this embodiment, the heating unit can be designed smaller, which is an advantage in terms of space as well as equipment costs.

It will be understood that the flash vapour and the carbamate dissociation vapour, which both comprise ammonia and carbon dioxide, will be processed so as to, ultimately, be returned to the urea synthesis section as reactants. To this end, said outlets for flash vapour and carbamate dissociation vapour each are connected via a condensation and recirculation circuit to the urea synthesis section. The various design options for one or more condensers, possible decomposers and further condensers, are known to the person skilled in the field of urea production.

Besides the specific set up of an MP or LP section comprising a flashing unit and an ammonia and carbon dioxide liberating unit, the urea production zone can be designed in accordance with the options known and available to the skilled person. Some embodiments of the system of the invention are discussed hereinafter.

The HP synthesis section generally comprises a HP stripper, a HP reactor and a HP carbamate condenser. The stripper is preferably a $CO_2$ stripper. The urea production zone comprises a liquid flow line from the reactor to the HP stripper. Optionally, the urea production zone provides for a parallel connection to an MP dissociator, by providing a second liquid flow line from the reactor to such MP dissociator.

The HP synthesis section comprises an inlet for $NH_3$ feed, for example at the HP carbamate condenser.

The reactor is configured for forming urea from $NH_3$ and $CO_2$ and has an outlet for urea synthesis solution. In $CO_2$ stripping plant the urea synthesis solution e.g. has an N/C ratio of 2.85 to 3.3 (in a conventional, non $CO_2$ stripping plant, the N/C ratio will be, e.g., 3-3.4). The reactor is operated at urea synthesis pressure, i.e. HP, and urea synthesis temperature, e.g. above 100 bar, for instance 120 to 300 bar, e.g. 120 to 200 bar; and/or for instance at a temperature of 160-240° C. and preferably at a temperature of 170-220° C. Example pressure ranges are 190° C.-200 bar for a so-called conventional plant, and 183° C.-145 bar for a $CO_2$ striping plant.

The reactor is for instance a vertical reactor with trays, wherein the feed inlet is at the bottom and the urea synthesis solution is withdrawn from an upper part of the vertical reactor, for instance using a down-comer.

The reactor for instance has a separate outlet for gas (so-called inerts). The inerts are supplied for instance as gas stream directly or indirectly to the preferred AN section. The inerts originate e.g. from the feed streams and include e.g. $N_2$. The gas stream from the gas outlet of the reactor comprises e.g. also $NH_3$.

The urea production zone may comprise one or more reactors in series, for instance a first reactor and an after-reactor. The urea production plant may also comprise one or more reactors in parallel.

The reactor and the HP carbamate condenser are optionally combined in a single vessel. An example is an integrated reactor/condenser as described in U.S. Pat. No. 5,767,313. An example integrated condenser/reactor comprises a reaction zone and a condensation zone combined in a single vessel. The condensation zone comprises for instance a heat exchanging surface, such as a tube bundle. The reaction zone comprises for instance baffles. The reaction zone is typically arranged downstream of the condensation zone in the vessel. An example integrated condenser/reactor is a submerged condenser (pool condenser) comprising a horizontal vessel and a tube bundle configured for receiving cooling fluid in the tubes and process medium in the vessel space.

The HP stripper has an inlet for $CO_2$ feed as strip gas and has an outlet for stripped urea solution, and an outlet for a gas stream. The plant is preferably of the $CO_2$ stripping type. The stripped urea solution comprising urea, water, carbamate and ammonia, and is supplied to said MP or LP flashing.

The HP carbamate condenser (HPCC) typically receives at least a part, preferably all, of the raw NH: feed. The HPCC receives at least a part, for instance all, of the gas stream from the HP stripper. The HP carbamate condenser has an outlet for a stream comprising the condensed carbamate connected to an inlet of the reactor, and in a combined condenser/reactor the condensation zone is in fluid connection with the reaction zone.

The urea production zone may comprise a $CO_2$ compressor to compress a $CO_2$ feed stream to urea synthesis pressure. The compressor is for instance a multi-stage compressor. The $CO_2$ is for example available at relatively low pressure (e.g. less than 20 bar) at battery limit, e.g. from a synthesis gas plant. The synthesis gas plant comprises for example a steam reformer, a water gas shift reactor, and a $CO_2$ removal unit. The synthesis gas plant may also produce $H_2$ used in an ammonia plant. The $NH_3$ feed of the urea plant may originate from said ammonia plant. Other sources of the $CO_2$ feed stream and NH: feed stream are also possible.

Generally, in the various embodiments of the invention, the HP stripper comprises for example a vertical shell-and-tube heat exchanger with an inlet for supplying urea solution to be stripped into the tubes, said inlet provided at the top of the stripper, and an outlet for stripped urea solution at the bottom, and an outlet for a mixed gas stream at the top of the stripper. The HP stripper is preferably of the $CO_2$ stripping type and has an inlet for $CO_2$ feed used as strip gas at the bottom. The mixed gas stream is condensed in the HP carbamate condenser into a high pressure recycle stream containing carbamate which is supplied to the reactor. In case of a combined reactor/condenser in a single vessel this may involve transport of condensate from a condensation section to a reactor section inside the vessel, in particular flow of carbamate-containing liquid from a condensation zone to a reaction zone inside the vessel.

The HP stripper is typically a device configured for counter-current contact of urea solution with a strip gas stream. Typically the HP stripper is configured with the urea solution and the strip gas stream in the tubes, while heat is supplied by steam on the shell side. In the invention, the HP stripper uses all or a part of the raw $CO_2$ feed as strip gas. The stripping action with $CO_2$ as strip gas causes a reduction of the N/C ratio of the urea solution. The stripped urea solution has an N/C ratio that is lower than the urea synthesis solution, e.g. an N/C ratio of less than 3.0, less than 2.7 or even less than 2.5, such as in the range 1.5-2.5 or in the range 2.0-2.5.

In the plants and processes of the invention, the HP carbamate condenser (HPCC) is for instance a shell-and-tube heat exchanger. The HPCC is for instance a vertical condenser or a horizontal condenser. A shell-and-tube heat exchanger as HPCC is operated with process medium (in particular, the gas to be condensed) in the shell side space and cooling fluid in the tubes, or with process medium in the tubes and cooling fluid in the shell side space.

In some embodiments, the HPCC is for instance a falling-film carbamate condenser with cooling fluid in the shell. In further embodiments, the HPCC is for instance a submerged condenser. The HPCC is for instance a shell-and-tube condenser with a horizontal U-shaped tube bundle, process medium in the shell side and with a submerged tube bundle, and is e.g. a pool condenser. The HPCC comprises e.g. a U-shaped tube bundle or a straight tube bundle. The HPCC is optionally a pool reactor, which comprises a pool condenser zone and a reactor zone. The pool reactor comprises for instance baffles in the shell space.

The HPCC for example also comprises an inlet for $NH_3$ feed to the shell space.

Preferably, the flashing unit, preferably an MP flashing unit, is configured for (substantially) adiabatic flashing. Preferably the flashing unit is a flash vessel.

Advantageously, by the preferred (substantially) adiabatically flashing from HP to MP in an MP flash vessel (MPF) the resulting MP gas stream (flash vapour) has a low $NH_3$:$CO_2$ molar ratio, such as lower than 2.0, e.g. in the range 0.8-1.2, and/or lower than the N/C ratio of the HP stripped urea solution. The flash vapour may advantageously have a relatively high $CO_2$ concentration such that the MP condensation section may operate at a more advantageous N/C ratio.

In some embodiments, $NH_3$ and $CO_2$ are removed from the urea solution in the MP flash vessel in a molar ratio $NH_3$ to $CO_2$ of less than 2.0, such as a molar ratio in the range of 0.8-1.2. The first MP gas stream may have an even lower molar ratio $NH_3$ to $CO_2$ if $CO_2$ is added to the gas stream.

The MP or LP treatment unit generally comprises a gas/liquid separation zone, e.g. in the preferred flash vessel, e.g. by said zone or flash vessel having a top outlet for gas and a bottom outlet for liquid, wherein the liquid is urea solution.

The preferred adiabatic nature of the flash in the preferred MP flash vessel advantageously contributes to a low N/C ratio (molar ratio $NH_3$ to $CO_2$) of the formed gas stream. In particular, upon adiabatic pressure reduction $CO_2$ leaves the urea solution from the $CO_2$ HP stripper to a higher degree than $NH_3$.

The flash vapour has an N/C molar ratio (molar ratio $NH_3$ to $CO_2$) of preferably less than 2.0, e.g. 0.5-1.5, such as 0.9-1.2, e.g. about 1.0. The flash vapour contains $NH_3$ and $CO_2$ in a molar ratio of preferably less than 2.0, e.g. 0.5-1.5, such as 0.9-1.2, e.g. about 1.0. The first gas stream contains for instance about 40-50 wt. % $NH_3$, about 40-50 wt. % $CO_2$, and e.g. 10-20 wt. % $H_2O$; these ranges may also apply to the components removed from the liquid phase of the urea solution in case of $CO_2$ being added to the flash vapour. The flash vapour as received by the MP carbamate condenser, i.e. at the inlet of the condenser, preferably has such N/C molar ratio (molar ratio $NH_3$ to $CO_2$), and preferably contains for instance about 40-50 wt. % $NH_3$, about 40-50 wt. % $CO_2$, and e.g. 10-20 wt. % $H_2O$.

The preferred MP heater (MP dissociator MPD) has an inlet for high pressure off-gas received from the melamine synthesis section. The MPD is typically a heat exchanger normally (and in addition to the hot melamine off-gases) using a heating fluid, for example steam, for indirect heat exchange for dissociating carbamate that is comprised in the urea synthesis solution. The use of steam as heating fluid in the MP dissociator provides the advantage of great flexibility to ensure sufficient carbamate removal from the urea solution, in particular independently of the N/C ratio at the inlet of the of the MP dissociator. The MP dissociator is for instance a shell-and-tube heat exchanger with steam in the shell and urea solution in the tubes. The MP dissociator comprises for instance a rectifying section arranged, for urea solution, upstream of the shell-and-tube heat exchanger part, the rectifying section being configured for gas/liquid separation of the urea solution expanded from HP to MP and counter-current contact between urea solution and a gas stream from the heat exchanging part. This contributes to good removal of carbamate from the urea solution.

The preferred medium pressure urea product stream, i.e., the MP urea solution at the outlet of the MP dissociator has for instance an N/C ratio of at least 4. The second MP gas stream from the MP dissociator has for instance an N/C ratio of at least 2.5.

In some embodiments, the MP dissociator also receives other urea solution streams, such as urea solution obtained indirectly from the HP stripper.

The carbamate dissociation vapour is supplied from the MP dissociator to an MP condensation section (MPCC). The MP condensation section has a liquid outlet for carbamate solution.

The urea production zone comprises a gas flow line for the flashed vapour directly or indirectly, preferably directly, to the MP condensation section such that at least part of said gas, preferably all, is transported as gas to the MP condensation section. In this way advantageously $CO_2$ contained in the stripped urea solution may be recovered using the MP condensation section.

In embodiments with the preferred (substantially) adiabatic flash, at least a part of the vapour from the flash can be used to correct (decrease) the N/C ratio in the MP condensation section. The combined carbamate condensation of the flash vapour and the carbamate dissociation vapour in the MP condensation section provides for optimum N/C ratio close to 2 of the formed condensate, i.e. carbamate solution. Thereby recovery of $CO_2$ in the form of carbamate solution is enabled. The carbamate condensation is also advantageously achieved at relatively higher temperature (higher condensation point) with the advantageous relatively low N/C ratio in the MP condensation section.

By virtue of the MP treatment unit, the $CO_2$ comprised in the flash vapour, which $CO_2$ originates from the HP stripper, can be used and recovered in the MP condensation section, such that the steam consumption of the HP stripper may be lower at constant stripping efficiency a. Thereby relatively more $CO_2$ can be supplied advantageously to the HP stripper. In preferred embodiments with an ammonia-consuming unit, e.g. the ammonium nitrate section, the HP stripper may advantageously operate with relatively lower stripping efficiency a compared to urea production sections only producing urea melt as $NH_3$ included in the stripped urea solution (also as carbamate) and received by the preferred LP dissociator can be used in the preferred ammonia-consuming unit, e.g. be reacted in the preferred ammonium nitrate section. The skilled person understands that in the context of urea plants, a lower stripping efficiency a, as that term is used in the art, can provide an advantage.

The MP condensation section comprises one or more MP carbamate condensers and has a liquid outlet for MP carbamate solution connected for instance to a recycle flow line to the HP synthesis section. The MP condensation section also comprises an outlet for non-condensed gas. The gas is supplied e.g. to an absorber or scrubber, or for instance to a neutralization section of an optional ammonium nitrate section.

The MP condensation section may comprise an MP carbamate condenser operated with a cooling fluid, e.g. a cooling liquid, such as cooling water, optionally as second MP carbamate condenser arranged downstream of a first MP carbamate condenser, wherein the first condenser is for instance heat integrated with a pre-evaporator. The second condenser is for instance a shell-and-tube heat exchanger. The second condenser receives for instance both vapour and liquid from the first MP carbamate condenser. The MP condensation section further comprises a gas/liquid separator, in particular for separating the carbamate solution from the non-condensed gas.

The MP condensation section preferably receives an aqueous stream, e.g. ammonia water, e.g. an aqueous stream from a waste water treatment section or for instance steam condensate. Thereby crystallization of carbamate is advantageously avoided. Optionally the MP condensation section receives for instance LP carbamate solution from an optional LP carbamate condenser if used.

The system for the production of urea and melamine described above can be designed as a new (grassroots) plant. It is also possible to provide the system by building a new melamine plant, to be connected to a pre-existing urea plant. Alternatively, the system comprises a new urea plant to be connected to a pre-existing urea plant. The system of the invention can also be provided by connecting a pre-existing urea plant and a pre-existing melamine plant. E.g., a pre-existing urea plant having an section comprising a flash unit and a heating unit for the dissociation of flashed urea liquid, can be provided with a melamine off-gas connection to said heating unit, preferably an MP heating unit. A pre-existing urea plant not having an MP or LP flash can be modified so as to be provided with an MP or LP flash unit and an ammonia and carbon dioxide liberating unit, such as an MP heater, for dissociating flashed urea liquid, as well as with a connection so for melamine off-gas to such MP heater. Moreover, the invention relates to modifying (revamping) a pre-existing system for the combined or integrated production of urea and melamine. E.g., a pre-existing system comprising connected HP melamine and urea production zones, and having a connection of melamine off-gas to the urea production zone, such as to an MP condensation section of the urea production zone, can be provided with a connection for melamine off-gas (in lieu of the aforementioned connection or possibly in addition thereto) to an ammonia and carbon dioxide liberating unit in an MP or LP section, preferably an MP section, of the urea production zone, provided (or to be provided) with a flash unit, preferably an MP flash unit, for sending flashed urea liquid to said ammonia and carbon dioxide liberating unit. Also, a pre-existing system comprising connected HP melamine and urea production zones, and having a connection of melamine off-gas to a HP urea synthesis section, can be modified by adding a flash unit plus heater, preferably an MP flash plus heater, as described hereinabove, and providing a melamine off-gas connection to said heater in lieu of the aforementioned connection or possibly in addition thereto.

The invention is further illustrated hereinafter with reference to the non-limiting drawings. In these drawings, numbered reference signs indicate equipment parts ("units") and letters indicate process streams ("streams") as follows.
Units:
  1 HP urea synthesis section
  2 HP melamine synthesis section
  3 Flashing unit
  4 Ammonia and carbon dioxide liberating unit
  5 LP recovery section
  6 MP condensation section
  7 Packed bed
Streams:
  a urea synthesis solution
  b HP melamine off-gas
  c flash vapour
  d flashed urea liquid
  e', e" ammonia and carbon dioxide vapours
  f MP urea product solution
  g LP carbamate solution
  h LP urea product stream In FIG. 1 it is shown that a urea synthesis solution (a) coming from a HP urea synthesis section (1), is subjected to flashing in an MP flashing unit (3). This results in a flash vapour, i.e., an ammonia and carbon dioxide vapour (e') which is removed, and a flashed urea liquid (d). The flashed urea liquid is sent to an upper inlet of an MP heating unit, i.e., an ammonia and carbon dioxide liberating unit (4). This unit is typically a shell-and tube heat exchanger in which, at the shell side, heat can be provided, typically by means of a heat exchange fluid, such as steam or a hot condensate ("HEAT"), which exits the unit after having exchanged heat ("exHEAT"). In accordance with the present invention, off-gases (b) from a high-pressure melamine plant (2) are sent to the MP heating unit (tube side) and therein are brought into contact, counter-currently, with the flashed urea liquid. The heating of the flashed urea liquid results in decomposition of ammonium carbamate present in the flashed urea liquid, and consequently liberation of ammonia and carbon dioxide vapour (e"), which is removed with the aforementioned flash vapour. The urea liquid from which the decomposed carbamate has been removed, is obtained as an MP urea product solution (f). Depending on the sensible heat available from the melamine off-gas, and the heat requirement in the MP heating, unit, the application of heat exchange fluid can be reduced or abandoned, or it can be fully used, in conjunction with the heat provided by the melamine off-gas. This reflects general possibilities for conducting to the invention, and further holds for all of the figures.

Figure 2:
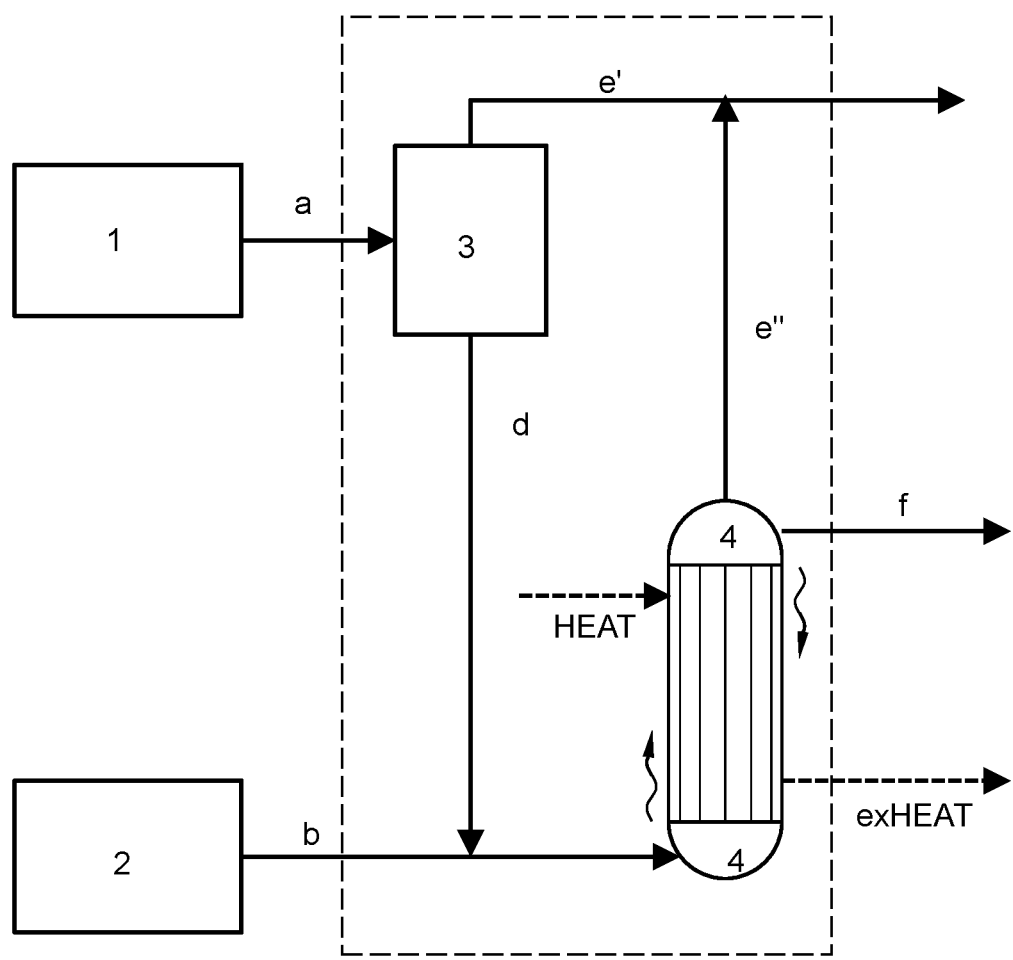

In FIG. 2 it is shown that a urea synthesis solution (a) coming from a HP urea synthesis section (1) is subjected to flashing in an MP flashing unit (3). This results in a flash vapour, i.e., an ammonia and carbon dioxide vapour (e') which is removed, and a flashed urea liquid (d). The figure further shows a HP melamine synthesis section from which HP melamine off-gas (b) is obtained. The flashed urea liquid (d) and the melamine off-gas (b) are combined and sent to a lower inlet of an MP heating unit, i.e., an ammonia and carbon dioxide liberating unit (4). This unit is typically a shell-and tube heat exchanger in which, at the shell side, heat can be provided, typically by means of heat exchange fluid such as steam or a hot condensate ("HEAT"), which exits the unit after having exchanged heat ("exHEAT"). In accordance with the present invention, the flashed urea liquid (d) is led through the MP heating unit (tube side). By having been brought into contact with the hot melamine off-gases (b), and optionally also with heat from a heat exchanging fluid, ammonium carbamate contained in the flashed urea liquid is subjected to decomposition, and consequently to liberation of ammonia and carbon dioxide vapour (e"), which is removed with the aforementioned flash vapour. The urea liquid from which the decomposed carbamate has been removed, is obtained as an MP urea product solution (f).

Figure 3:
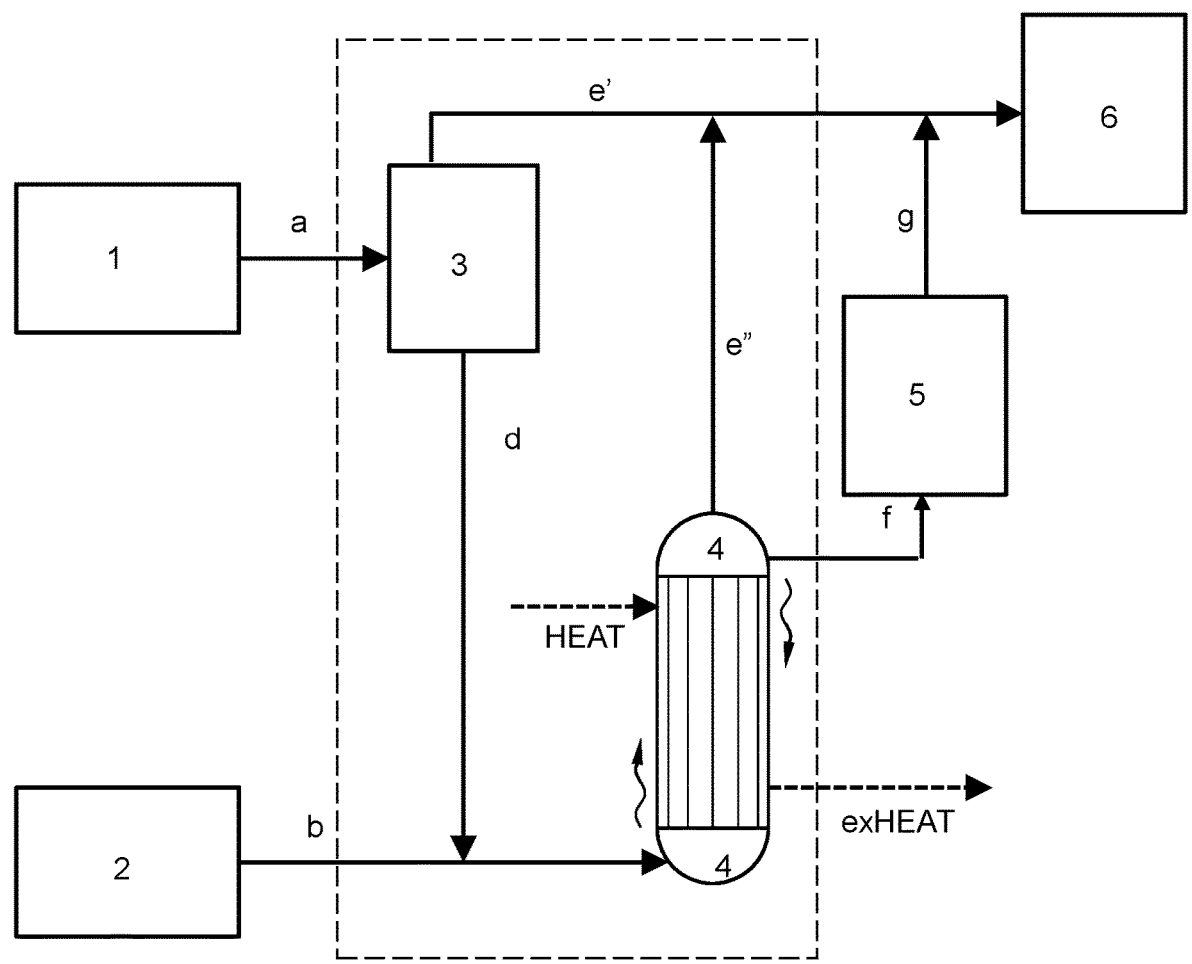

FIG. 3 shows the same set-up as FIG. 2, with the same description applicable. In addition, the figure shows that the MP urea product solution (f) is sent to a low-pressure recovery section (5). From said section an LP urea product stream (h) is obtained, and an LP carbamate solution (g). The latter is sent to (via a pump, not shown) to an MP condensation section (6) in which it is combined with condensate of the ammonia and carbon dioxide vapours (e' and e"), to form MP carbamate (not shown).

Figure 4:
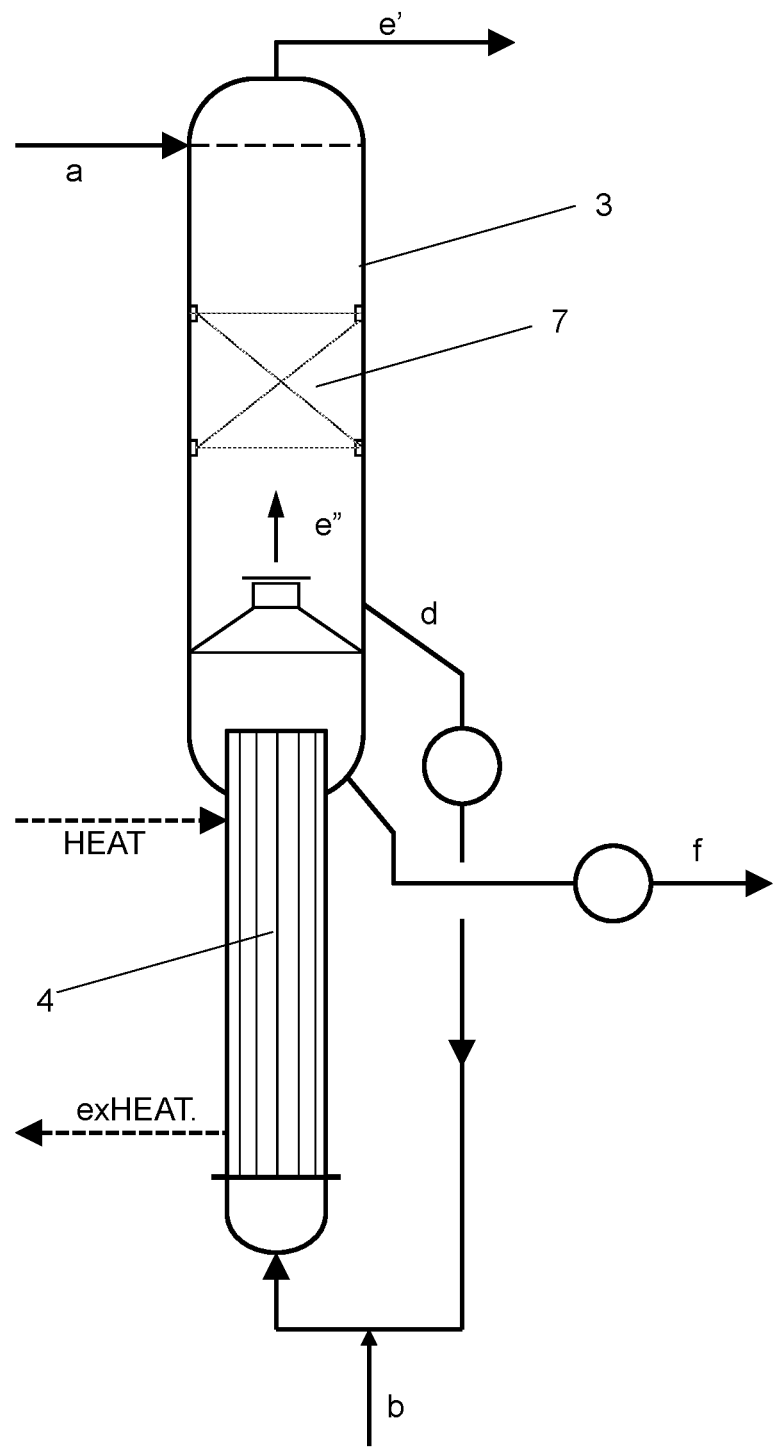
FIG. 4 and FIG. 5 are schematic drawings representing the application of a single flashing and heat exchanging apparatus in a system for the production of urea and melamine.
Figure 5:
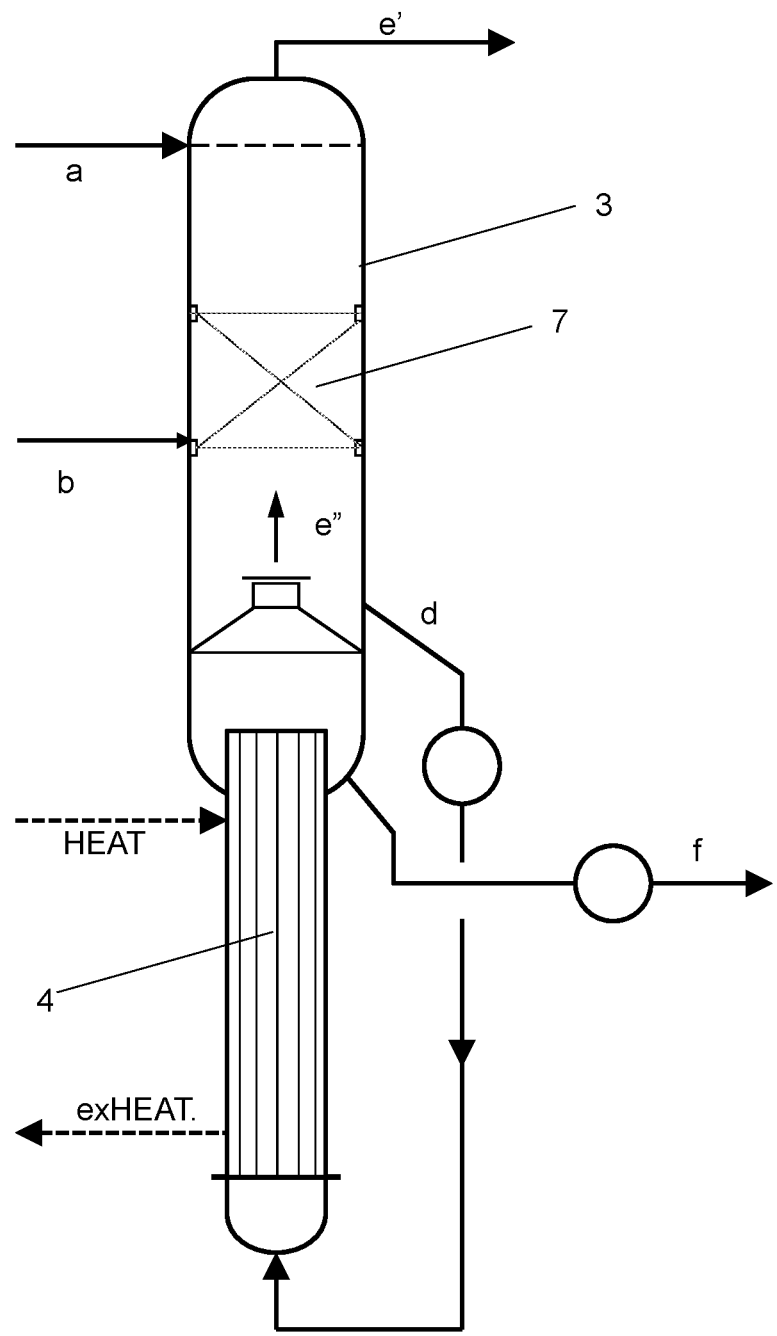

FIG. 4 shows a single flashing and heating apparatus that can be used in operating the present invention. Shown is a urea synthesis solution (a) entering the apparatus via an upper inlet. In a flashing unit (3) of the apparatus, the urea solution is subjected to flashing. This results in a flash vapour, i.e., an ammonia and carbon dioxide vapour (e') which is removed on top of the apparatus, and a flashed urea liquid (d). The latter is led over a packed bed (7), and sent to a bottom inlet of the apparatus. It is further shown that a HP melamine off-gas (b) is combined with the flashed urea liquid, after which the combined stream enters the apparatus via a bottom inlet. This is a lower inlet of an MP heating unit, i.e., an ammonia and carbon dioxide liberating unit (4). This unit is typically a shell-and tube heat exchanger in which, at the shell side, heat can be provided, typically by means of heat exchange fluid such as steam or a hot condensate ("HEAT"), which exits the unit after having exchanged heat ("exHEAT"). In accordance with the present invention, the flashed urea liquid (d) is led through the MP heating unit (tube side). By having been brought into contact with the hot melamine off-gases (b), and optionally also with heat from a heat exchanging fluid, ammonium carbamate contained in the flashed urea liquid is subjected to decomposition, and consequently to liberation of ammonia and carbon dioxide vapour (e"), The ammonia and carbon dioxide vapour (e") is sent across the packed bed (7), thereby acting as a stripping agent for the flashed urea liquid (d), and is removed with the flash vapour (e') on top of the apparatus.

The invention claimed is:

1. A process for the production of urea and melamine, wherein the production of urea comprises subjecting ammonia and carbon dioxide to a urea-forming reaction in a high-pressure urea synthesis section so as to obtain a high pressure urea synthesis solution, subjecting the urea synthesis solution to flashing, resulting in a flash vapour comprising ammonia and carbon dioxide, and a flashed urea liquid; subjecting the flashed urea liquid to treatment so as to obtain a urea product solution and a carbamate recovery vapour, said treatment comprising one or more ammonia and carbon dioxide liberating steps, thereby removing ammonia and carbon dioxide vapour from the flashed urea liquid, wherein the production of melamine comprises subjecting urea to a non-catalytic, high pressure melamine forming reaction, so as to obtain melamine and a melamine off-gas vapour comprising ammonia and carbon dioxide; and wherein the combined process comprises contacting at least part of the melamine off-gas with the flashed urea liquid before or during at least one of said ammonia and carbon dioxide liberating steps.

2. The process according to claim 1, wherein the flashing is conducted at medium pressure, and comprising subjecting the flashed urea liquid to treatment in a medium pressure treatment section, so as to obtain a medium pressure urea product solution, and a medium pressure carbamate recovery vapour.

3. The process according to claim 1, wherein at least part of the high pressure urea synthesis solution is obtained from subjecting an effluent from the urea-forming reaction to high pressure stripping.

4. The process according to claim 3, wherein the high pressure stripping is by applying carbon dioxide as a stripping medium.

5. The process according to claim 1, wherein the flash vapour and the carbamate recovery vapour are subjected to condensation so as to form a carbamate solution, and subjecting said carbamate solution to recirculation to the high pressure synthesis section.

6. The process according to claim 5, wherein a carbamate liquid obtained from melamine synthesis is combined with at least one carbamate solution.

7. The process according to claim 1, comprising subjecting the urea product solution to recovery of still present ammonia and carbon dioxide at low pressure, obtaining a low pressure carbamate solution and a low pressure urea product stream.

8. The process according to claim 1, wherein obtaining a medium pressure urea product stream comprises medium pressure stripping.

9. The process according to claim 8, wherein the medium pressure stripping is by applying carbon dioxide as a stripping medium.

10. The process according to claim 1, wherein at least part of the produced urea is the urea that is subjected to the melamine forming reaction.

11. The process according to claim 1, comprising contacting the melamine off-gas vapour in a counter-current manner with the flashed urea liquid.

12. The process according to claim 1, wherein the melamine off-gas vapour contacted with the flashed urea liquid has a temperature of 150° to 300° C.

13. The process according to claim 12, wherein the melamine off-gas vapour contacted with the flashed urea liquid has a temperature of 200° C. to 250° C.

14. A system for the production of urea and melamine, said system comprising a urea production zone; said urea production zone comprising a high pressure urea synthesis section and, downstream thereof and in fluid communication therewith, a urea recovery section adapted to separately obtain a urea solution and a carbamate recovery stream; the system further comprising a melamine production zone; said melamine production zone comprising a high pressure melamine synthesis section, said production zones being connected with each other so as to allow transport of melamine off-gas obtained from the melamine synthesis section to the urea production zone, whereby the urea production zone comprises a medium or low pressure treatment section adapted to receive said melamine off-gas, said treatment section comprising a flashing unit and at least one ammonia and carbon dioxide liberating unit, said flashing unit having an inlet for urea synthesis solution connected to an outlet of the high pressure synthesis section via a pressure reducing device, an outlet for flash vapour and an outlet for flashed liquid, said ammonia and carbon dioxide liberating unit having an inlet for flashed liquid connected to the outlet for flashed liquid from the flashing unit, an outlet for carbamate recovery vapour and an outlet for a urea product stream, said outlets for flash vapour and carbamate recovery vapour each being connected via a condensation and recirculation circuit to the urea synthesis section, wherein an outlet for melamine off-gas vapour from the melamine synthesis section is in fluid communication with an inlet of at least one ammonia and carbon dioxide liberating unit, allowing the melamine off-gas vapour to be contacted with flashed liquid in or upstream of the ammonia and carbon dioxide liberating unit.

15. The system according to claim 14, wherein the urea production zone comprises an outlet for urea connected to an inlet of the melamine synthesis section.

16. The system according to claim 14, wherein the flashing unit and the heating unit are connected via a rectifying column.

17. The system according to claim 16, wherein the rectifying column comprises a packed bed, and wherein an outlet for melamine off-gas vapour from the melamine synthesis section is in fluid communication with an inlet of the rectifying column positioned such to allow the off-gas vapour to flow across the packed bed.

18. The system according to claim 16, wherein an outlet for melamine off-gas vapour from the melamine synthesis section is in fluid communication with an inlet of the heating unit.

19. The system according to claim 18, wherein the outlet for melamine off-gas vapour from the melamine synthesis section is in fluid communication with an inlet of the heating unit and is positioned at a lower end thereof.

20. The system according to claim 16, wherein the flashing unit and the heating unit are connected via a rectifying column and are contained in a single apparatus.

21. The system according to claim 14, wherein said treatment section comprising a flashing unit and at least one ammonia and carbon dioxide liberating unit is a heating unit.

22. A method for the modification of a pre-existing urea plant comprising a high pressure urea synthesis section and, downstream thereof and in fluid communication therewith, a urea recovery section adapted to separately obtain a urea solution and a carbamate recovery stream, the method comprising connecting the urea plant with a melamine plant comprising a high pressure melamine synthesis section so as to allow recirculation of melamine off-gas from the melamine off-gas treatment section to the urea plant, the method comprising adding a medium or low pressure treatment section adapted to receive said melamine off-gas, said treatment section comprising a flashing unit and at least one ammonia and carbon dioxide liberating unit, said flashing unit having an inlet for urea synthesis solution connected to an outlet of the high pressure synthesis section via a pressure reducing device, an outlet for flash vapour and an outlet for flashed liquid, said ammonia and carbon dioxide liberating unit having an inlet for flashed liquid connected to the outlet for flashed liquid from the flashing unit, an outlet for carbamate recovery vapour and an outlet for a urea product stream, said outlets for flash vapour and carbamate recovery vapour each being connected via a condensation and recirculation circuit to the urea synthesis section, wherein an outlet for melamine off-gas vapour from the melamine synthesis section is in fluid communication with an inlet of the ammonia and carbon dioxide liberating unit, allowing the melamine off-gas vapour to be contacted with flashed liquid in or upstream of the ammonia and carbon dioxide liberating unit.

23. The method according to claim 22, comprising providing a connection between an outlet for urea from the urea production zone to an inlet of the melamine synthesis section.

24. A method for the modification of a pre-existing system for the production of urea and melamine, said pre-existing system comprising a urea production zone and a melamine production zone; said urea production zone comprising a high pressure urea synthesis section in fluid communication with a urea recovery section adapted to separately obtain a urea solution and a carbamate recovery stream, said recovery section comprising a medium or low pressure treatment section comprising a flashing unit and an ammonia and carbon dioxide liberating unit, said flashing unit having an inlet for urea synthesis solution connected to an outlet of the high pressure synthesis section via a pressure reducing device, an outlet for flash vapour and an outlet for flashed liquid, said ammonia and carbon dioxide liberating unit having an inlet for flashed liquid connected to the outlet for flashed liquid from the flashing unit, an outlet for carbamate recovery vapour and an outlet for a urea product stream, said outlets for flash vapour and carbamate recovery vapour each being connected via a condensation and recirculation circuit to the urea synthesis section, said melamine production zone comprising a high pressure melamine synthesis section and, downstream thereof and in fluid communication therewith, a melamine off-gas treatment section for obtaining melamine off-gas of reduced pressure; said production zones being connected with each other so as to allow transport of melamine off-gas from the melamine off-gas treatment section to the urea production zone, and optionally also to allow transport of urea from the urea production zone to the melamine synthesis section, the method comprising providing a connection between an outlet for melamine off-gas vapour from the melamine synthesis section to an inlet of the ammonia and carbon dioxide liberating unit, allowing the melamine off-gas vapour to be contacted with flashed liquid in or upstream of the ammonia and carbon dioxide liberating unit.

* * * * *